(12) United States Patent
Xin et al.

(10) Patent No.: US 9,190,099 B2
(45) Date of Patent: Nov. 17, 2015

(54) HIGHER ORDER STRUCTURED DYES WITH ENHANCED OPTICAL FEATURES

(75) Inventors: Meiguo Xin, Gainesville, FL (US); Vincent Jo Davisson, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 324 days.

(21) Appl. No.: 13/634,795

(22) PCT Filed: Mar. 15, 2011

(86) PCT No.: PCT/US2011/028528
§ 371 (c)(1),
(2), (4) Date: Nov. 14, 2012

(87) PCT Pub. No.: WO2011/115995
PCT Pub. Date: Sep. 22, 2011

(65) Prior Publication Data
US 2013/0052746 A1    Feb. 28, 2013

Related U.S. Application Data

(60) Provisional application No. 61/314,038, filed on Mar. 15, 2010.

(51) Int. Cl.
G01N 21/00    (2006.01)
G11B 7/246    (2013.01)
B82Y 10/00    (2011.01)
C09B 11/24    (2006.01)

(52) U.S. Cl.
CPC ............... *G11B 7/246* (2013.01); *B82Y 10/00* (2013.01); *C09B 11/24* (2013.01); *G11B 2007/24624* (2013.01)

(58) Field of Classification Search
None
See application file for complete search history.

(56) References Cited

U.S. PATENT DOCUMENTS 5,051,504 A * 9/1991 Hahn et al. .................. 544/58.6

OTHER PUBLICATIONS

Hernado, J. et al. Excitonic Behavior of Rhodamine Dimers: A Single-Molecule Study, 2003, J. Phys. Chem., vol. 107, pp. 43-52.*
Ambroise, A. et al., Design and Synthesis of Porphyrin-Based Optoelectronic Gates, American Chemical Society, Chem. Mater., 2001, 13, 1023-1034.
Rezig, H. et al., Feasibility of Optically Controlled Integrated Mach-Zehnder Device Based on Azo Dye—Doped PMMA Thin Films, Elsevier Science, Optics Communication, Dec. 15, 2001, 200, 261-269.
Deryugin, L.N. et al., Investigation of a Thin-Film Rhodamine 6G Laser Logic Element, Izvestiya VUZ. Radioelektronika, 1980, vol. 23, No. 8, pp. 70-76.

(Continued)

*Primary Examiner* — Robert Xu
(74) *Attorney, Agent, or Firm* — Purdue Research Foundation

(57) ABSTRACT

Organic dyes that are covalently bonded multimers or higher order symmetrical structures where one or more dye units may optionally contain deuterium substitutions are disclosed. The disclosed dyes are particularly useful for optical coatings, new optical nanomaterials, high density storage devices. The structural and optical characteristics of the disclosed dyes provide avenues for increased information-content through surface-enhanced Raman resonance spectroscopy.

19 Claims, 5 Drawing Sheets

(56) References Cited

OTHER PUBLICATIONS

Leng, W. et al., Resonance Raman Intensity Analysis of Merocyanine Dimers in Solution, American Chemical Society, J. Phys. Chem. B, 2004, 108, 10284-10294.

Knudsen, G. M. et al., Quantification of Isotope Encoded Proteins in 2-D Gels Using Surface Enhanced Resonance Raman, American Chemical Society, Bioconjugate Chem., 2008, 19, 2212-2220.

Deb., S.K. et al., Detection and Relative Quantification of Proteins by Surface Enhanced Raman Using Isotopic Labels, American Chemical Society, J. Am. Chem. Soc., 2008, 130, 9624-9625.

Lu, L. et al., Exciton and Charge—Transfer Interactions in Nonconjugated Merocyanine Dye Dimers: Novel Solvatochromic Behavior for Tethered Bichromophores and Excimers, American Chemical Society, J. Am. Chem Soc., 1999, 121, 8146-8156.

Xiyan, Z. et al., Preparation and Third Order Nonlinear Optical Property of Rhodamine—6G Doped $SiO_2$—$TiO_2$ sol—Gel Thin Films, Link: http://proceedings.spiedigitallibrary.org/, 1998.

Shinozaki, R. et al., Humidity—Dependent Reversible Aggregation of Rhodamine 6G Dye Immobilized within Layered Niobate $K_4Nb_6O_{17}$, American Chemical Society, Langmuir, 2004, 20, 7583-7588.

Deb, S. K. et al, Accurate Concentration Measurement Using Surface—Enhanced Raman and Deuterium Exchanged Dye Pairs, Society for Applied Spectroscopy, 2008, vol. 62, No. 9, 1001-1007.

Faulds, K. et al., SERRS as a more Sensitive Technique for the Detection of Labelled Oligonucleotides Compared to Fluorescence, The Royal Society of Chemistry, Analyst, 2004, 129, 567-568.

Cao, Y. C. et al., Raman Dye-Labeled Nanoparticle Probes for Proteins, American Chemical Society, J. Am. Chem. Soc. 2003, 125, 14676-14677.

Deryugin, L. N. et al, Thin—Film Rhodamine 6G Waveguide Laser with a Corrugated Substrate, American Institute of Physics, Sov. J. Quant. Electron., 1976, vol. 5, No. 9, 1129-1130.

Sasai, R. et al., Aggregated Structures of Rhodamine 6G Intercalated in a Fluor-Taeniolite Thin Film, American Chemical Society, Langmuir, 2002, 18, 6578-6583.

Garcia, O. et al., Synthetic Strategies for Hybrid Materials to Improve Properties for Optoelectronic Applications, Adv. Funt. Mater., 2008, 18, 2017-2025.

Innocenzi, P. et al., Dimer—to—Monomer Transformation of Rhodamine 6G in Sol—Gel Silica Films, Journal of Non-Crystalline Solids, 1996, 201, 26-36.

Bell, S. E. J. et al., Quantitative Surface—Enhanced Raman Spectroscopy of Dipicolinic Acid—Towards Rapid Anthrax Endospore Detection, The Royal Society of Chemistry, Analyst, 2005, 130, 545-549.

Kuimova, M. K. et al., Intramolecular Rotation in a Porphyrin Dimer Controls Singlet Oxygen Production, American Chemical Society, J. Am. Chem. Soc., 2009, 131, 7948-7949.

Abu Hatab, N. A. et al., Surface-Enhanced Raman Spectroscopy Substrates Created via Electron Beam Lithography and Nanotransfer Printing, American Chemical Society, ACSNano, 2008, vol. 2, No. 2, 377-385.

Krafft, C., Bioanalytical Applications of Raman Spectroscopy, Anal Bioanal Chem., 2004, 378, 60-62.

Lawson, E. E. et al., Biomedical Applications of Raman Spectroscopy, Journal of Raman Spectroscopy, 1997, Vo. 28, 111-117.

Sanchez-Valencia, J. R. et al., Incorporation and Thermal Evolution of Rhodamine 6G Dye Molecules Adsorbed in Porous Columnar Optical $SiO_2$ Thin Films, American Chemical Society, Langmuir, 2009, 25, (16), 9140-9148.

Pantelic, N. et al., Dynamics of Rhodamine 6G Sorption into a Porous Tri-Block Copolymer Thin Film, American Chemical Society, J. Phys. Chem. C., 2007, 111, 18595-18604.

Campion, a. et al., Surface—Enhanced Raman Scattering, Chemical Society Reviews, 1998, vol. 27, 241-250.

Martinez, V. et al., Characterization of Rhodamine 6G Aggregates Intercalated in Solid Thin Films of Laponite Clay. 1. Absorption Spectroscopy, American Chemical Society, J. Phys. Chem. B, 2004, 108, 20030-20037.

Walter, M.G. et al., Syntheses and Optoelectronic Properties of Amino/Carboxyphenylporphyrins for potential use in dye-sensitized $TiO_2$ Solar Cells, J. Porphyrins Phthalocyanines, 2007, 11, 601-612.

Vogel, R. et al., Dimer—to—Monomer Transformation of Rhodamine 6G in Aqueous PEO—PPO—PEO Block Copolymer Solutions, American Chemical Society, Macromolecules, 2002, 35, 2063-2070.

Hungerford, G. et al., Comparison of the Fluorescence Behaviour of Rhodamine 6G in Bulk and Thin Film Tetraethylorthosilicate Derived Sol-Gel Matrices, Journal of Photochemistry and Photobiology A: Chemistry, 1999, 129, 71-80.

Streltsov, S. A. et al., The Hoechst 33258 Covalent Dimer Covers a Total Turn of the Double—Stranded DNA, Journal of Biomolecular Structure & Dynamics, 2006, vol. 24, Iss. No. 3, 285-302.

Mohammadnezhad, J. et al., Synthesis and Characterization of Monomer and Dimer Complexes of Porphyrin Iron (III) with Bridging Phenylcyanamide Ligands, Inorganica Chimica Acta, 2009, 362, 2782-2787.

Igarashi, K. et al., Dominant Factors of Preventing Rhodamine 6G from Dimer Formation in Aqueous Solutions, Bull. Chem. Soc. Jpn., 1999, 72, 1197-1202.

Christie, R.J. et al. Optical Properties and Application of a Reactive and Bioreducible Thiol-Containing Tetramethylrhodamine Dimer, American Chemical Society, Bioconjugate Chem., 2009, 20, 476-480.

Cunningham, D. et al., Practical Control of SERRS Enhancement, The Royal Society of Chemistry, Faraday Discuss., 2006, 132, 135-145.

Ilich, P. et al., Direct Observation of Rhodamine Dimer Structures in Water, Elsevier, Spectrochimica Acta Part A, 1996, 52, 1323-1330.

Romieu, A. et al. "Postsynthetic Derivatization of Fluorophores with alpha-Sulfo-beta-alanine Dipeptide Linker. Application to the Preparation of Water Soluble Cyanine and Rhodamine Dyes" Bioconjugate Chemistry, Dec. 15, 2007, vol. 19, No. 1, pp. 279-289.

Liu, Y. et al. "Spectrophotometric Study on the Controlling Factor of Molecular Selective Binding of Dyes by Bridged Bis(beta-cyclodextrin)s with Diselenobis(benzoyl) Linkers", The Journal of Physical Chemistry B, Apr. 30, 2005, vol. 109, No. 21, pp. 10717-10726.

Hernando, J. et al. "Excitonic Behavior of Rhodamine Dimers: A Single Molecule Study," The Journal of Physical Chemistry A, Dec. 6, 2002, vol. 107, No. 1, pp. 43-52.

Lee, L. G. et al. "New energy transfer dyes for DNA sequencing" Nucleic Acids Research, Jul. 14, 1997, vol. 25, No. 14, pp. 2816-2822.

Strachan, J.-P. et al. "Synthesis and Characterization of Tetrachlorodiarylethyne-Linked Porphyrin Dimers. Effects of Linker Architecture on Intradimer Electronic Communication," Inorganic Chemistry, Mar. 3, 1998, vol. 37, No. 6, pp. 1191-1201.

Zeena, S. et al. "Conformational Switching and Exciton Interactions in Hemicyanine-Based Bichromophores," Journal of the American Chemical Society, Jul. 20, 2001, vol. 123, No. 32, pp. 7859-7865.

Johansson, M. K. et al. "Intramolecular Dimers: A New Design Strategy for Fluorescence-Quenched Probes" Chemistry—A European Journal, Aug. 4, 2003, vol. 9, No. 15, pp. 3467-3471.

* cited by examiner

HIGHER ORDER STRUCTURED DYES WITH ENHANCED OPTICAL FEATURES

CROSS-REFERENCE TO RELATED APPLICATION

This application is the §371 U.S. National Stage of International Application No. PCT/US2011/028528, filed Mar. 15, 2011, which claims the benefit of U.S. Provisional Application Serial Nos. 61/314,038, filed on Mar. 15, 2010, each of which is incorporated by reference herein in its entirety.

BACKGROUND

1. Technical Field

This disclosure relates to new organic dyes that are covalently bonded multimers or higher order symmetrical structures in which one or more dye units may optionally contain deuterium substitutions. The disclosed dyes may be particularly useful for optical coatings, new optical nanomaterials, high density storage devices. The structural and optical characteristics of the disclosed dyes provide avenues for increased information-content through surface-enhanced Raman resonance spectroscopy.

2. Description of the Related Art

Reactive fluorescent dyes have many important applications including photonic technology, specifically as active media within systems requiring syntonizable lasers, photo- and opto-electronic devices such as solar energy conversion, microscopic non-linear optical devices, and molecular probes in biochemical systems. Commonly used fluorescent dyes include, but are certainly not limited to Rhodamine (R6G), Crystal Violet (CV), and Nile Blue. Other dyes and their synthetic derivatives have been studied in optoelectronic devices include cyanin, ruthenium-based dyes, isophorone derivatives, perylene dyes, anthracene dyes, BODIPY dyes, porphyrin and Azoaromatic polymers.

Among those fluorescent dyes, R6G has been widely studied and applied for thin film lasers. For example, R6G has been incorporated into transparent and porous $SiO_2$ thin films. The resulting R6G/SiO2 composite thin films do not disperse light and therefore can be used for integration into optical and photonic devices. A high order of R6G non-covalent dimers has been observed during the aggregation process of R6G laser dye intercalated in supported thin films of Laponite clay.

Some fluorescent and non-fluorescent dye dimers that display unique optical properties have been studied in various areas. For example, synthesized porphyrin dimers showed efficient electron injection into $TiO_2$ in dye-sensitized solar cell based energy conversion. Hoechst dimers have also been prepared and shown to either bind dsDNA or form bridges between two dsDNA chains. Tethered merocyanine dimers displayed novel solvatochromic effects compared to the corresponding monomers. Recently, a reactive and bioreducible thiol-containing tetramethylrhodamine dimer was synthesized and proved useful as a dithiol reduction-sensitive fluorescent probe in cellular tracking systems as well as a thiol-based dye labeling reagent.

On the other hand, Raman spectroscopy is becoming an increasingly practical technique because of its minimal sample preparation requirements and compatibility with biological materials in aqueous solutions. Raman spectroscopy is the measurement of the wavelength and intensity of scattered light from molecules. The Raman scattered light occurs at wavelengths that are shifted from the incident light by the energies of molecular vibrations related to the overall polarization of the system. Typical applications are in structure determination, multi-component qualitative analysis, and quantitative analysis.

More recently, Surface-enhanced resonance Raman spectroscopy (SERRS) has become an attractive technique for applications in protein, nucleic acid, and related biomarker analysis because of its unprecedented signal enhancement. For example, R6G derivatives, as monomers, have been prepared and applied to Surface Enhanced Resonance Raman Spectroscopy (SERRS) for accurate quantification of protein concentration. Accurate quantification of protein content and composition has been achieved using isotope-edited surface enhanced resonance Raman spectroscopy (IERS). The spectral signatures reflect the expected statistical distribution of isotopologue labels incorporated into proteins in a gel matrix format without interference from protein features. However, during technology transfer to an industrial setting, these R6G monomer dyes have suffered shortcomings. The interactions between R6G and nanoparticles are variable and difficult to control, which renders their Raman signals difficult to repeat. The conjugation between the R6G monomer dye, linker, and target protein is sensitive to sample conditions. Therefore, development of new R6G derivatives that can overcome shortcomings of the monomeric forms in SERRS is an urgent task for the development of IERS.

Although R6G dimer formation in solvent has been widely studied, R6G dimer aggregation has also been observed when dyes are intercalated in solid supported thin films. Covalently linked R6G molecules have not been synthesized and their optical properties in film coating and Raman spectroscopy have not yet been characterized. The optical industry has recently indicated that R6G dimers exhibit properties desirable for certain optical coating applications; for example, extremely high absorption in the light band from 500 nm to 600 nm is needed. Development of properties to meet industrial needs is therefore desirable.

Hence, there is a need for new dyes with enhanced optical features. Moreover, there is a need for new dyes that can be used as optical coatings. Finally, there is a need for new dyes as optical coatings with stronger association to substrate surfaces.

SUMMARY OF THE DISCLOSURE

In satisfaction of the aforementioned needs, a multimer of an organic dye compound is disclosed. The multimer may include at least two molecules of the organic dye compound covalently coupled together through a linker. The disclosed multimer may be a dimer, trimer, tetramer, or other high order structures. The multimer may be used in optical coatings to characterize the surface of a substrate upon which the multimer is deposited. The disclosed multimer may have a higher order of symmetry than corresponding monomeric dye compound. The composition may also have stronger association to the substrate than optical coatings based on corresponding monomeric dye compound.

The multimerized dye compound may be an R6G multimer in which two or more R6G dye molecules are covalently coupled together through a linker. The R6G multimer may have superior optical properties to R6G monomers. The structure of the linker may be optimized to enhance both self-associated inter- and intra-molecular interactions. In addition, use of linkers to provide higher order symmetrical structures such as trimers and tetramers to provide additional optical enhancements may also be achieved.

As discussed earlier, the disclosed multimers have not been synthesized or applied in the fields of optical coating and Raman based bioanalysis. Moreover, the disclosed multimerized dye compound may include identical or different R6G dye monomers. One or both monomers can include deuterium substitutions. If both monomers contain deuterium substitutions, the substitution patterns can be either the same or different. Deuterium substitutions on one or both monomer units in symmetrical or asymmetrical patterns will cause changes in the Raman resonance signature.

Spectral features of these multimers are similar to, but differ from the constituent R6G monomers in intensity and sensitivity. The new R6G dimers described herein are not only different in structure from their corresponding monomers, but also differ in certain spectral features, the binding affinities to anions and metals surfaces including the binding kinetics. These materials have potential to fulfill needs as optical coatings to take advantage of the novel light absorbing properties. The compositions described here show exceptionally high molar extinction coefficients and high fluorescence emission providing utility as film coatings.

The new dimers have unique interactions with metallic nanoparticles of gold and silver that create new materials in three dimensional matrices such as PVDF. These materials create plasmonic surfaces that provide enhanced Raman signals beyond those observed with the monomeric dyes Improved chemical and physical stability of these materials have been observed using these Raman signals as an indicator.

Linker designs provide options for incorporation of multiple functional groups suitable for subsequent covalent attachment to surfaces (nanomaterials or plastics/polymers), proteins, or nucleic acids. This feature makes these exceptionally "bright" dyes useful as fluorescence labels or Raman based sensors. The capacity of these higher order dye structures to provide stronger and more consistent surface enhanced Raman signatures provides a significant advancement of technology for biomolecule detection.

According to another aspect of the present disclosure, a method of enhancing Raman resonance spectroscopic signatures of an organic dye compound is also disclosed. The method may include the steps of forming a multimer of the organic dye compound and subjecting the multimer to Raman resonance spectroscopy, wherein the multimer comprises at least two molecules of the organic dye compound covalently coupled together through a linker. The method may further include the steps of aggregating the multimer with metallic nanoparticles and/or depositing the multimer on a substrate.

Other advantages and features of the disclosed material and its application will be described in greater detail below. Although only a limited number of embodiments are disclosed herein, different variations will be apparent to those of ordinary skill in the art and should be considered within the scope of this disclosure.

BRIEF DESCRIPTION OF THE DRAWINGS

For a more complete understanding of the disclosed composition and its application, reference should be made to the embodiments illustrated in greater detail in the accompanying drawings, wherein.

Figure 1:
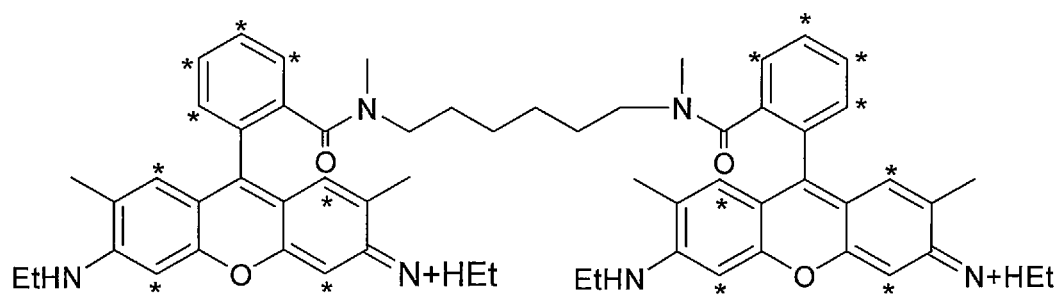
FIG. 1 is a graphic illustration of the chemical structure of a dye based on R6G dimer according to one aspect of this disclosure.

It should be understood that the drawings are not necessarily to scale and that the disclosed embodiments are sometimes illustrated diagrammatically and in partial views. In certain instances, details which are not necessary for an understanding of the disclosed process or which render other details difficult to perceive may have been omitted. It should be understood, of course, that this disclosure is not limited to the particular embodiments illustrated herein.

DETAILED DESCRIPTION OF THE DISCLOSURE

As used herein to describe the compounds, compositions, methods and processes of the present application, the following terms have the following meanings, unless otherwise indicated:

The term "Rhodamine" refers to any compound that comprises a parent Rhodamine ring or an extended Rhodamine, including any substituted versions of the same, wherein substitutions can be made at any one or all of 1-, 2-, 2'-, 4-, 4'-, 5-, 5'-, 7-, 7'-, 8-, and 9-carbons and/or at any one or both of the exocyclic amino and imino moieties.

The term "multimer" refers to a compound that comprises at least two molecules coupled together, such as through a linker covalently bonded to the molecules.

The term "dimer" refers to a compound that comprises two molecules coupled together, such as through a linker covalently bonded to both molecules.

The term "trimer" refers to a compound that comprises three molecules coupled together, such as through a linker covalently bonded to all three molecules.

The term "tetramer" refers to a compound that comprises four molecules coupled together, such as through a linker covalently bonded to all four molecules.

The term "derivative" refers to a compound that is substituted at one or more locations.

The term "biomolecule" refers to a molecule of a type typically found in a biological system, whether such molecule is naturally occurring or the result of some external disturbance of the system (e.g., a disease, poisoning, genetic manipulation, etc), as well as synthetic analogs and derivatives thereof.

The term "isotopomer(s)" (isotopic isomers) refers to isomers having the same number of each isotopic atom but differing in their positions.

The term "isotopologue(s)" refers to versions of the same molecular structure that contain different numbers of an isotopic atom. For example, there can be three carbon isotopologues of ethanol: $C^{12}$ in both carbon positions, $C^{13}$ in one position and $C^{12}$ in the other, or $C^{13}$ in both positions. By contrast, the two versions that contain $C^{13}$ in either the first or second carbon position are "isotopomers", as defined above.

The term "alkyl" means a hydrocarbon group that may be linear, cyclic, or branched or a combination thereof having the number of carbon atoms designated (i.e., C.sub. 1-8 means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicycle[2.2.1]heptanes, bicycle[2.2.2] octane, etc. Alkyl groups can be substituted or unsubstituted, unless specifically indicated. Examples of substituted alkyl groups include haloalkyl, thioalkyl, aminoalkyl, and the like.

The term "alkenyl" means a hydrocarbon group that contains at least one carbon-to-carbon double bond. The term "alkynyl" means a hydrocarbon group that contains at least one carbon-to-carbon triple bond. Alkenyl and alkynyl groups can be substituted or unsubstituted, unless specifically indicated.

The term 'substituent" means an atom or a group that replaces another atom or group in a molecule.

The term "ring" means a compound whose atoms are arranged in a cyclic form. The ring compound can be either carbocyclic or heterocyclic.

The term "heterocyclyl" or "heterocyclic", which are used synonymous herein, means a saturated or unsaturated nonearomatic ring containing 5-10 atoms (preferably 5 or 6) in which at least one is a heteroatom selected from nitrogen, oxygen or sulfur (typically 1 to 5 heteroatoms). The heterocyclic ring may be monocyclic (with preferably 5 or 6 atoms) or bicyclic (with preferably 9 or 10 atoms). Examples of heterocyclic groups include pyrrolidine, piperidine, imidazolidine, pyrozolidine, butyrolactam, valerolactam, imidazolidinone, hydantoin, dioxolane, phthalimide, piperidine, 1-4-dioxane, morpholine, thiomorpholine, thiomorpholine-5-oxide, thiomorpholine-S—S-dioxide, piperazine, pyran, pyridine, 3-pyrroline, thiopyran, pyrone, tetrahydrofuran, tetrahydrothiophene, quinuclidine.

All of the above terms, in some embodiments, include both substituted and unsubstituted forms of the indicated groups. These groups may be substituted multiple times, as chemically allowed.

In general, this disclosure is related to a composition comprising at least one covalent dimer of a dye compound. The disclosed composition may be used as an optical coating to characterize the surface of a substrate upon which the composition is coated. The composition may have a higher order of symmetry and/or stronger association to the substrate than optical coatings based on corresponding monomeric dye compound. The covalent dimer may have a generic formula of dye—linker—dye.

Exemplary dye compound suitable for use in this disclosure include, but are not limited to, organic dyes with different sites for optional isotopic substitution of deuterium for one or more hydrogen atoms. The organic dyes include xanthene dyes like rhodamine and fluorescein, triarylmethane dyes like Crystal Violet, azo dyes like benzotriazole azo, mercaptopyridine. Dimers may be obtained by coupling reaction of two dye monomers in the presence of coupling reagents (i.e., O-(Benzotriazol-1-yl)-N,N,N',N'-tetramethyluronium hexafluorophosphate). The isotopic substitution employed in those dyes can be obtained through the use of isotopically substituted precursors of the dye-forming reaction. The isotopic variants may also be obtained by isotopic exchange of the labile aromatic protons of the chromophore by heating the dye in a deuterated acidic medium prior to incorporation into a dimer.

In a non-limiting embodiment of this disclosure, the covalent dimer may be two Rhodamine 6G monomers coupled together through a linker. The dimer may be used as reagents for covalent modification of target biomolecules. A general formula of the covalent dimer in this embodiment may be:

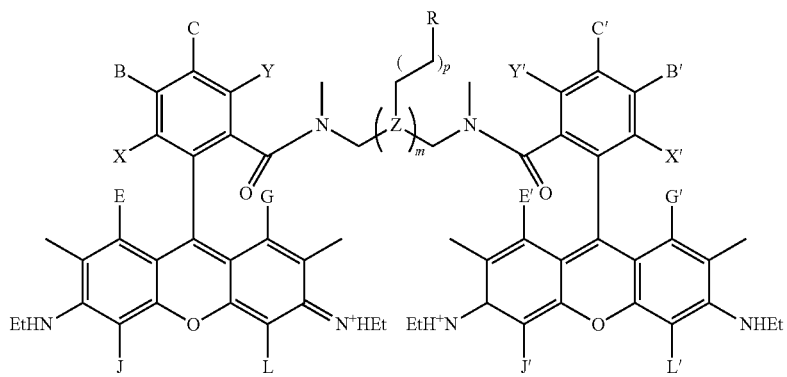

wherein R is either a halogen or —C(O)NR, the latter allowing linkage to other molecules such as proteins, nucleic acids, etc., and where m and p are numbers from 2-20 indicating a carbon chain in which heteroatoms such as S, O and N can be included, and where B, C, X, Y, E, G, J, L, as well as B', C', X', Y', E', G', J', L' are each independent hydrogen, deuterium, or halogen substituents, and where Z is CH, N, or B.

In a refinement of this embodiment, the linker may be a six-carbon bridge between the carboxylic acid moieties of each monomer, as illustrated in FIG. 1. The bridge may be aliphatic, or it may incorporate additional heteroatom such as S, O, or N, so long as the symmetry of the dimer is undisturbed. The length of the bridge can be varied. For example, the bridge may be an aliphatic chain containing a backbone of 4-15 methylene groups (—CH2-) in some embodiments. In other embodiments, the bridge may include a plurality of methylene groups interspersed at one or more intervals with heteroatom(s) including, but not limited to N, O, and S. Each nitrogen heteroatom may be further substituted by one or two hydrogens, phenyl, alkyl groups, or other functional groups with 1 to 6 carbons, in which the substitutions do not disturb the overall symmetry of the dimer.

In another non-limiting embodiment of this disclosure, the dimer of the present disclosure is based on Crystal violet with the following formula. The dimer may be used as reagents for covalent modification of target biomolecules:

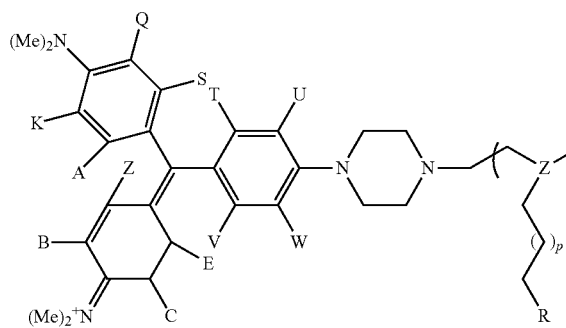 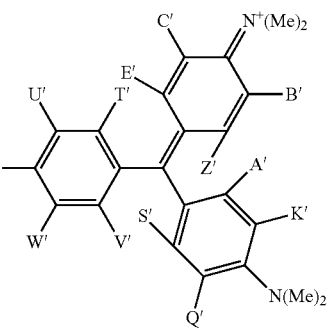

where R is either a halogen or —C(O)NR, the latter allowing linkage to other molecules such as proteins, nucleic acids, etc., and where m and p are numbers from 2-20 indicating a carbon chain in which heteroatoms such as S, O and N can be included, and where A, B, C, X, Y, E, K, Q, S, T, U, V, W as well as B', C', X', Y', E', K', Q', S', T' U' V' W' are each independent hydrogen, deuterium or halogen substituents, and where Z is CH, N, or B. BRIDGE typically has the formula: A-NH—(CH2)m-C (<CH2>xOR)—(CH2)n-NH—B, where m, n, and x are 1-10 (preferably 1-4) and R is COOH or its derivatives. The bridge can contain other heteroatoms (i.e., N, O, S) or hetrocycles. A and B are alkyl or alkenyl groups.

In a refinement of this embodiment of this disclosure, the covalent dimer may have the exemplary structure below.

the symmetry of the dimers. The Rhodamine 6G or Crystal Violet can be substituted in deuterated forms according know processes, such as those disclosed in PCT Application No. PCT/US2005/034795. In addition, the dimers may also subject to isotopic substitutions to alter the symmetry of the overall molecule in some embodiments.

It is to be understood that the present disclosure may be expanded beyond dimerized compounds. Trimers or tetramers of the organic dye compounds may also be prepared and used in light of this disclosure. For trimeric structures, the bridging unit may contain a central atom that can be substituted with three identical linkers for dye attachment and define a central element of symmetry. For tetrameric structures the bridging unit contains a central element of symmetry

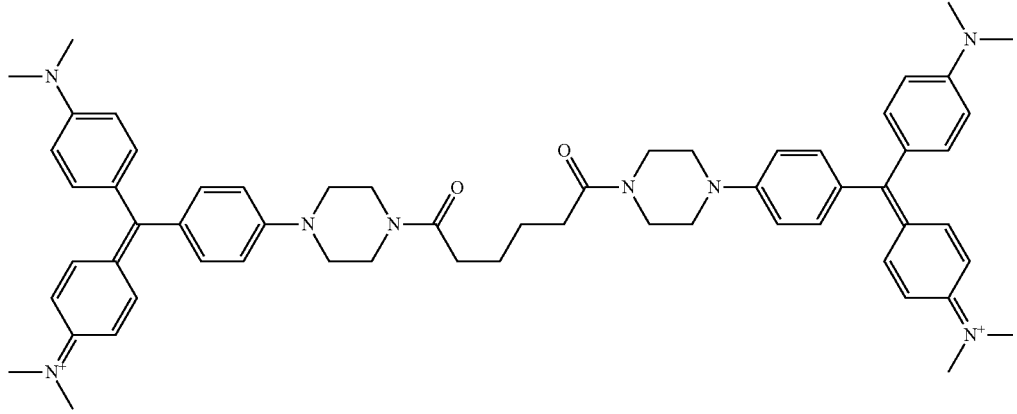

The bridge in this refinement may be aliphatic, or it may incorporate additional heteroatom such as S, O, or N, so long as the symmetry of the dimer is undisturbed. The length of the bridge can be varied. For example, the bridge may be an aliphatic chain containing a backbone of 4-15 methylene groups (—CH2-) in some embodiments. In other embodiments, the bridge may include a plurality of methylene groups interspersed at one or more intervals with heteroatom(s) including, but not limited to N, O, and S. Each nitrogen heteroatom may be further substituted by one or two hydrogens, phenyl, alkyl groups, or other functional groups with 1 to 6 carbons, in which the substitutions do not disturb the overall symmetry of the dimer.

The organic dye compounds used in this disclosure may also be substituted in deuterated form to benefit from the features of the isotopomers and isotopologues, such as Raman active labeling, while minimizing the disturbance to that can be substituted with four identical linkers for dye attachment and define a central element of symmetry.

Synthesis and Application

Molecules that absorb light in the visible to near-IR region with high Raman cross-sections are core elements of the materials. Examples for this disclosure include organic dyes with different sites for isotopic substitution of deuterium for one or more hydrogen atoms. The organic dyes include xanthene dyes like rhodamine and fluorescein, triarylmethane dyes like Crystal Violet, azo dyes like benzotriazole azo, mercaptopyridine. Dimers can be obtained by coupling reaction of two dye monomers in the presence of coupling reagents (i.e., O-(Benzotriazol-1-yl)-N,N,N',N'-tetramethyluronium hexafluorophosphate). The isotopic substitution employed in those dyes can be obtained through the use of isotopically substituted precursors of the dye-forming reaction. The isotopic variants may also be obtained by isotopic exchange of the labile aromatic protons of the chromophore by heating the dye in a deuterated acidic medium prior to incorporation into a dimer.

All solvents and reagents were purchased from Aldrich. Reactions were monitored by thin layer chromatography (TLC) using precoated gel plates (60 F254). Column chromatography was performed using 230-400 mesh silica gel. The dyes obtained commercially were further purified by flash column chromatography using a dichloromethane/methanol mixture both before and after isotopic exchange. $^1$H NMR spectra were acquired on a 300, 400 or 500 MHz spectrometer. The chemical shifts of the protons are given in parts per million (ppm) with respect to tetramethylsilane as internal standard. High resolution mass spectra were obtained using electrospray ionization.

Synthesis of N,N'-Bis(6-carboxyl-Rhodamine 6G)-N,N'-dimethyl-1,6-hexyl diamide: To a solution of R6G (43 mg, 0.1 mmole) in DMF was added O-(Benzotriazol-1-yl)-N,N,N',N'-tetramethyluronium hexafluorophosphate (45 mg, 0.11 mmole) and $Et_3N$ (20 mg, 0.2 mmole). After 20 minutes, N,N'-dimethyl-1,6-hexanediamine (7 mg, 0.048 mmole) was added, and the mixture was stirred overnight at room temperature. The reaction was quenched with diluted HCl and extracted with a 2:1 mixture of isopropanol and dichloromethane. The mixture was washed with diluted HCl, brine, and water, and then dried over $Na_2SO_4$. Liquid chromatography of the crude product with dichloromethane and methanol produced the desired product as a deep red solid (52 mg, 0.055 mmole, 55% yield). H1 NMR ($CD_3OD$): δ1.05 (m, 4H), 1.44 (m, 4H), 2.11 (t, J=14 Hz, 2H), 2.15 (t, J=14 Hz, 2H), 2.17 (br, s 12H), 3.01 (br, s, 6H), 3.12 (t, J=13 Hz, 2H), 3.15 (t, J=13 Hz, 2H), 3.52 (q, J=13 Hz, 3H), 3.56 (q, J=13 Hz, 3H), 6.91 (m, 4H), 7.05 (m, 4H), 7.51 (m, 2H), 7.65 (m, 2H), 7.75 (m, 4H). M+ calcd 938.5459. found 938.5456.

Synthesis of D4-Rhodamine 6G-(6-carboxymethyl)-N-methyl-N'-methyl-hexyl amide: To a solution of D4-Rhodamine 6G-6-[carboxy-(N-hydroxysuccimidyl)]-N-methyl)-hexyl amide (28 mg, 0.05 mmole) in dry THF (5 ml) was added methylamine (1.0 mmole in THF). The reaction was stirred for 2 hours. Liquid chromatography of the mixture with dichloromethane and methanol (1% to 5% methanol) produced the desired product as a red solid (22 mg, 80% yield). $^1$H NMR ($CD_3OD$): δ1.05 (m, 4H), 1.44 (m, 8H), 2.11 (t, J=14 Hz, 2H), 2.17 (br, s 12H), 2.98 (s, 3H), 3.16 (t, J=13 Hz, 2H), 3.53 (q, J=13 Hz, 3H), 3.67 (s, 3H), 6.91 (s, 2H), 7.05 (s, 2H). M+ calcd 559.3586. found 559.3588.

Preparation of Dye Sample and Application to Membrane

Raman spectra were recorded by absorbing aliquots of different concentrations (i.e., 1 pM, 1 μM, 10 μM) R6G dye derivatives (1 μl of each sample) on Millipore PVDF membrane that were pre-soaked with MeOH. Dot-blot apparatus was applied for loading the dye material on PVDF membrane that has been pre-soaked with methanol. The membrane was coated with BBI gold and silver solutions.

Application of Gold Nanoparticles

Apply gold nanoparticles (i.e., PROTOGOLD, BBI Inc.) to the analyte with a volume (about 5-10 ml) that can incubate the membrane completely, the membrane in gold solution was covered to protect from light, and put on a slow shaker (20-50 rpm) until staining was visibly apparent. The gold particles can be commercial PROTOGOLD solution in which the size of nanoparticles is within 20-40 nm.

Application of Silver Nanoparticles

Apply silver enhancement solution until the stained color changed from dark red to dark brown; dry overnight with slow shaking (20-50 rpm). The silver particles are made in house by combining two silver solution (A:B=1:1, BBI Inc.) that including an afterward treatment of commercial silver enhancement kit solution. The size of the silver particle size is usually bigger than 40 nm, and the silver staining time is less than 5 minutes.

Evaluation of Enhanced Optical Features

UV absorbance spectra of D0-R6G monomer and D0-R6G dimer

Figure 2:
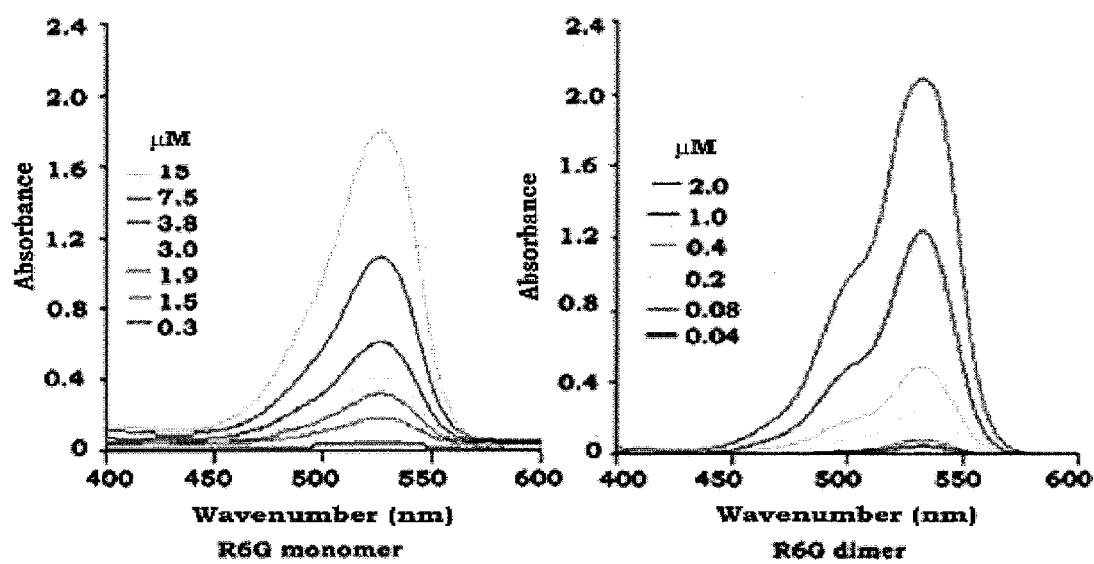
FIG. 2 is absorption spectra of the R6G dimer illustrated in FIG. 1 and its corresponding R6G monomer.

Visible absorbance spectra of D4-R6G monomer (D4=four H deuterated) and D0-R6G dimer (D0=non-deuterated) are illustrated in FIG. 2. Both dyes were dissolved in methanol, and spectra were recorded on a Cary 4 UV-Vis spectrophotometer. As indicated in FIG. 2, the UV absorbance spectrum of the R6G dimer is different from that of the R6G monomer. While the D4-R6G monomer displays a UV spectrum with maximum absorption at 527 nm, the UV spectrum of D0-R6G dimer has an apparent shoulder in addition to the maximum absorption at 533 nm. The shoulder spreads to shorter wavelengths as the dye concentration increases. UV absorbance of D4-R6G monomer did not show shoulders at any concentration. When dissolved in MeOH, the R6G dimer tends to form various aggregates, whereas the R6G monomer does not. The shoulder of the D0-R6G dimer may indicate different aggregation states of the dye. The calculated molar extinction coefficient of the D0-R6G 1 R6G dimer is $1.206 \times 10^6$ $M^{-1}$ $cm^{-1}$, whereas that of the D4-R6G monomer is $1.16 \times 10^5$ $M^{-1}$ $cm^{-1}$. Thus, dimerization has increased absorbance by an order of magnitude.

Fluorescence spectra of D4-R6G dimer and D0-R6G monomer

Figure 3:
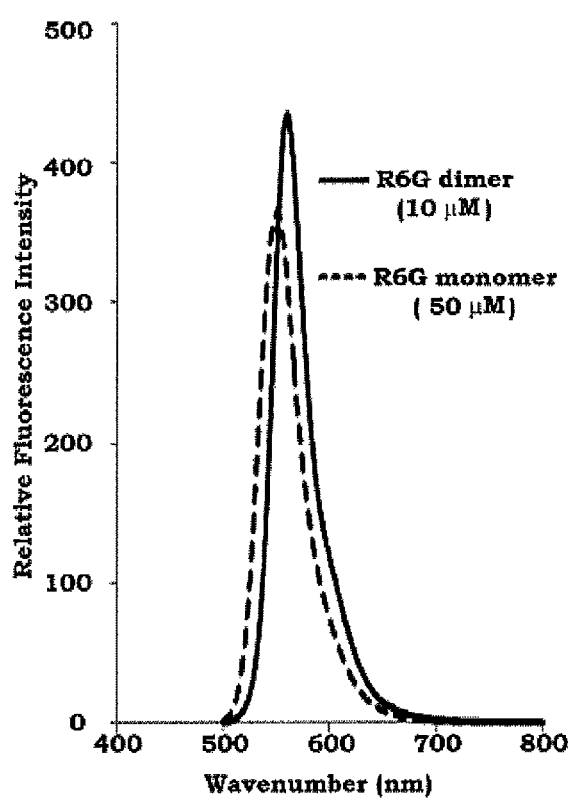
FIG. 3 is fluorescence spectra of the R6G dimer illustrated in FIG. 1 and its corresponding R6G monomer.

Normalized fluorescence emission spectra are shown in FIG. 3 for the D0-R6G dimer and D4-R6G monomer. Both dyes were dissolved in methanol, and spectra were recorded on a Cary Varian fluorescence spectrophotometer. The concentration of D0-R6G dimer (10 μM) and D4-R6G monomer (50 μM) were chosen for similar intensity values at the fluorescence emission peak wavelength and overlaid for comparison. The lower fluorescence noise apparent within the D0-R6G dimer Raman signals necessitated checking its fluorescence intensity and comparing it to that of the D4-R6G monomer. As shown in FIG. 3, the D0-R6G dimer has higher emission absorption (450 at 559 nm) at 10 μM, compared to D4-R6G monomer emission (350 at 550 nm) at 50 μM. A reference fluorescent spectrum of D0-R6G monomer was added; its emission is more close to the D4-R6G monomer.

SERS and SERRS of D0-R6G dimmer and D4-R6G monomer

A simple method was developed to evaluate Raman dyes on PVDF membrane. First, dissolve a dye in MeOH at specific concentrations (i.e., 1 μM); Second, dot-blot the solvent on PVDF membrane and dry; Third, gold and silver staining of the blots, then record Raman signals. This pure dye evaluation method is comparable to the protocol we developed for protein quantification on PVDF membrane The Raman spectra of both D0-R6G dimer and D4-R6G monomer are recorded with same instrumental setting (i.e. 1 coaddition, 10 s integration) with laser of 532 nm and 630 nm.

Samples for Raman spectral analysis were prepared by absorbing aliquots of 1.0 μM R6G dye derivatives on Millipore PVDF membrane that was pre-soaked with MeOH. The membrane was then coated with gold and silver nanoparticles solutions (British BioCell International). SERRS spectra were obtained using a Senterra Raman system with 532 nm argon ion excitation lasers (delivering 0.2 mW at the sample). The Raman signal was collected using a 20× Olympus objective coupled to a spectrograph with a fiber bundle for detection with a liquid nitrogen-cooled CCD. The integration time for all measurements was 10 s with a co-addition factor of 1.

Figure 4:
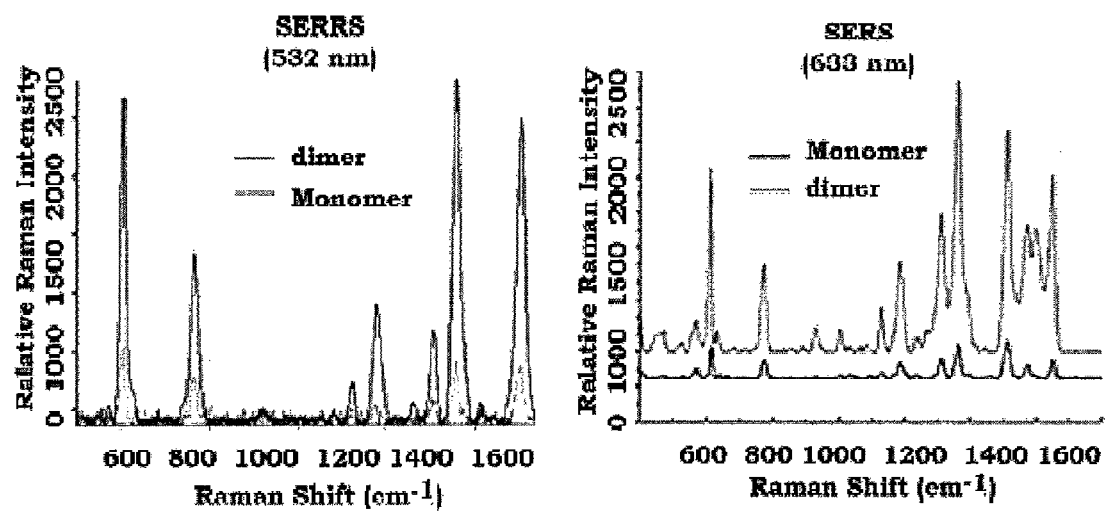
FIG. 4 is a Surface Enhanced Raman spectroscopy (SERS) and a Surface Enhanced Resonance Raman spectroscopy (SERRS) of the R6G dimer illustrated in FIG. 1 and its corresponding R6G monomer.

As shown in FIG. 4, Both SERS and SERRS of R6G dimmer displayed much intensive peaks (5-10 times based on the integration of 600 nm peak), compared to those of R6G monomer. On the other hand, the raw Raman spectra of R6G dimer showed quenched Fluorescence noise compared to those of R6G monomer.

Stability study of SERRS of D0-R6G dimmer and D4-R6G monomer

Figure 5:
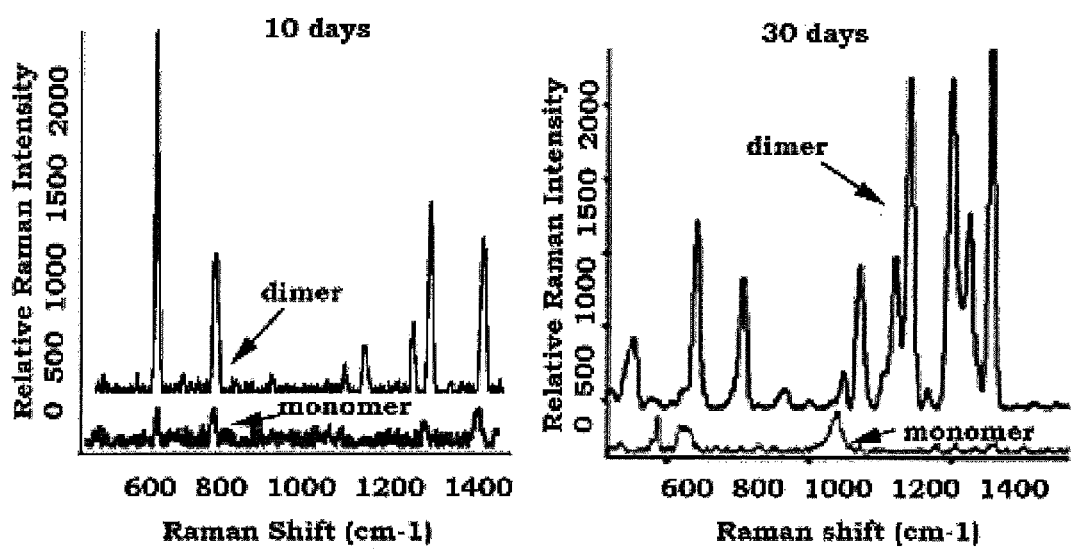
FIG. 5 is a stability study of Raman signals of the R6G dimer illustrated in FIG. 1 and its corresponding R6G monomer.

The SERRS of R6G dimer and monomer obtained in FIG. 4 was further tested for their stability. The membrane containing both spots was placed in dark for additional 10 and 30 days. SERRS of both days were recorded under same instrumental settings as described. As shown in FIG. 5, the SERRS signals of R6G monomer were gradually faded, and completely disappeared after 10 days; however, the SERRS signals of R6G dimer sustained after 10 or 30 days, although there were some intensity changes in its signals as well as appearance of some additional peaks, which may indicate a particular interation of R6G dimer with the nanoparticles on PVDF membrane.

INDUSTRIAL APPLICABILITY

The organic dyes disclosed herein include covalently bonded multimers or higher order symmetrical structures where one or more dye units may optionally contain deuterium substitutions. The disclosed dyes may be particularly useful for optical coatings, new optical nanomaterials, high density storage devices. The structural and optical characteristics of the disclosed dyes provide avenues for increased information-content through surface-enhanced Raman resonance spectroscopy.

While only certain embodiments have been set forth, alternatives and modifications will be apparent from the above description to those skilled in the art. These and other alternatives are considered equivalents and within the spirit and scope of this disclosure and the appended claims.

What is claimed is:

1. A multimer of an organic dye compound, the multimer comprising at least two molecules of the organic dye compound covalently coupled together through a linker having the general formula:

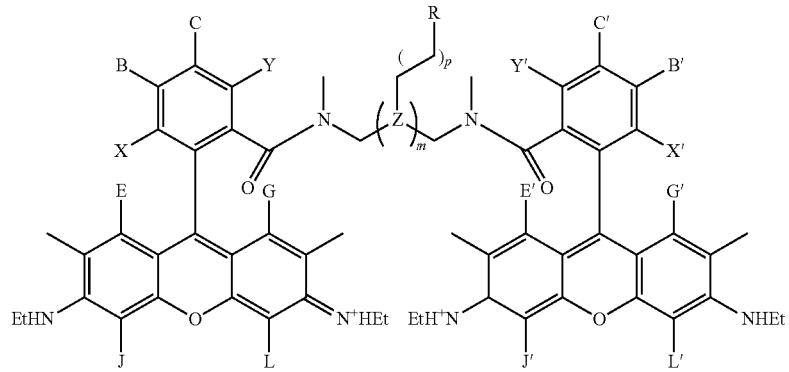

wherein R is a halogen and where m and p are numbers from 2-20 indicating a carbon chain in which heteroatoms such as S, O and N can be included, and where B, C, X, Y, E, G, J, L B', C', X', Y', E', G', J', and L' are each independent hydrogen, deuterium, or halogen substituents, and where Z is CH or N.

2. The multimer of claim 1, wherein the organic dye compound is selected from the group consisting of Rhodamine 6G and derivatives thereof.

3. The multimer of claim 1, wherein the organic dye compound is subject to one or more isotopic substitution.

4. The multimer of claim 3, wherein the isotopic substitution is deuteration.

5. The multimer of claim 1, wherein the multimer is a dimer.

6. The multimer of claim 1, wherein the multimer is a trimer or tetramer.

7. An aggregate of metallic nanoparticles and the multimer of claim 1.

8. The aggregate of claim 7, wherein the metallic nanoparticles are gold nanoparticles or silver nanoparticles.

9. A composite comprising a substrate and a multimer of claim 1 deposited on the substrate.

10. The composite of claim 9, further comprising metallic nanoparticles aggregated with the multimer on the substrate.

11. The composite of claim 9, wherein the substrate is a polyvinylidene fluoride membrane.

12. A coating for an optical surface, the coating comprising the multimer claim 1.

13. A method of enhancing Raman resonance spectroscopic signatures of an organic dye compound, the method comprising forming a multimer of the organic dye compound according to claim 1 and subjecting the multimer to Raman resonance spectroscopy.

14. The method of claim 13, further comprising the step of aggregating the multimer with metallic nanoparticles.

15. The method of claim 14, wherein the metallic nanoparticles are gold nanoparticles or silver nanoparticles.

16. The method of claim 13, further comprising depositing the multimer on a substrate.

17. The method of claim 16, wherein the substrate is a polyvinylidene fluoride membrane.

18. The method of claim 13, wherein the organic dye compound is selected from the group consisting of Rhodamine 6G and derivatives thereof.

19. The method of claim 13, wherein the organic dye compound is subject to one or more isotopic substitution.

* * * * *